United States Patent
Boeck et al.

(10) Patent No.: US 7,579,358 B2
(45) Date of Patent: *Aug. 25, 2009

(54) AEROSOL FORMULATION FOR INHALATION COMPRISING AN ANTICHOLINERGIC

(75) Inventors: Georg Boeck, Mainz (DE); Friedrich Schmidt, Ingelheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 90 days.

This patent is subject to a terminal disclaimer.

(21) Appl. No.: 10/935,502

(22) Filed: Sep. 7, 2004

(65) Prior Publication Data

US 2005/0101625 A1    May 12, 2005

Related U.S. Application Data

(60) Provisional application No. 60/513,862, filed on Oct. 23, 2003.

(30) Foreign Application Priority Data

Sep. 26, 2003   (DE) ................ 103 45 065

(51) Int. Cl.
*A61K 31/00* (2006.01)
*A61K 31/46* (2006.01)
*C07D 507/02* (2006.01)
*A61M 15/00* (2006.01)
*A61M 15/08* (2006.01)
*A61K 9/00* (2006.01)
*A61K 9/12* (2006.01)
*A61K 9/14* (2006.01)

(52) U.S. Cl. ............... 514/291; 546/91; 128/200.24; 128/202.17; 239/338

(58) Field of Classification Search ............ None
See application file for complete search history.

(56) References Cited

U.S. PATENT DOCUMENTS

| | | |
|---|---|---|
| 4,042,700 A | 8/1977 | Banholzer et al. |
| 4,608,377 A | 8/1986 | Banholzer et al. |
| 4,783,534 A | 11/1988 | Banholzer et al. |
| 5,610,163 A | 3/1997 | Banholzer et al. |
| 5,636,346 A | 6/1997 | Saxe |
| 5,654,314 A | 8/1997 | Banholzer et al. |
| 5,724,521 A | 3/1998 | Dedrick et al. |
| 5,770,738 A | 6/1998 | Banholzer et al. |
| 5,845,265 A | 12/1998 | Woolston |
| 5,918,010 A | 6/1999 | Appleman et al. |
| 5,920,854 A | 7/1999 | Kirsch et al. |
| 5,931,901 A | 8/1999 | Wolfe et al. |
| 5,952,505 A | 9/1999 | Banholzer et al. |
| 5,974,398 A | 10/1999 | Hanson et al. |
| 6,026,368 A | 2/2000 | Brown et al. |
| 6,044,375 A | 3/2000 | Shmueli et al. |
| 6,061,659 A | 5/2000 | Murray |
| 6,067,570 A | 5/2000 | Kreynin et al. |
| 6,078,866 A | 6/2000 | Buck et al. |
| 6,150,418 A * | 11/2000 | Hochrainer et al. ......... 514/630 |
| 6,223,163 B1 | 4/2001 | Van Luchene |
| 6,230,170 B1 | 5/2001 | Zellweger et al. |
| 6,247,009 B1 | 6/2001 | Shiiyama et al. |
| 6,253,189 B1 | 6/2001 | Feezell et al. |
| 6,269,361 B1 | 7/2001 | Davis et al. |
| 6,285,987 B1 | 9/2001 | Roth et al. |
| 6,298,348 B1 | 10/2001 | Eldering |
| 6,324,519 B1 | 11/2001 | Eldering |
| 6,336,132 B2 | 1/2002 | Appleman et al. |
| 6,421,675 B1 | 7/2002 | Ryan et al. |
| 6,455,524 B1 | 9/2002 | Bozung et al. |
| 6,486,321 B2 | 11/2002 | Banholzer et al. |
| 6,491,897 B1 | 12/2002 | Freund et al. |
| 6,506,900 B1 | 1/2003 | Banholzer et al. |
| 6,706,726 B2 | 3/2004 | Meissner et al. |
| 7,084,153 B2 * | 8/2006 | Banholzer et al. ........... 514/291 |
| 2001/0042064 A1 | 11/2001 | Davis et al. |

(Continued)

FOREIGN PATENT DOCUMENTS

CA       2425557 A1      4/2003

(Continued)

OTHER PUBLICATIONS

Chemical Abstract 122:204554, vol. 122, No. 17, Apr. 24, 1995—XP002192841 and XP 002192832.

(Continued)

*Primary Examiner*—Johann R Richter
*Assistant Examiner*—James H Alstrum Acevedo
(74) *Attorney, Agent, or Firm*—Michael P. Morris; Mary Ellen M. Devlin; Wendy A. Petka

(57) ABSTRACT

A pharmaceutical composition comprising:
(a) an active substance consisting of a compound of formula 1

$$\text{[structure of tiotropium-like cation with } X^- \text{ anion]} \quad 1$$

wherein $X^-$ is an anion;
(b) ethanol or a mixture of ethanol and water;
(c) a pharmacologically acceptable acid.

16 Claims, No Drawings

U.S. PATENT DOCUMENTS

| | | |
|---|---|---|
| 2001/0047297 A1 | 11/2001 | Wen |
| 2001/0051911 A1 | 12/2001 | Marks et al. |
| 2002/0002509 A1 | 1/2002 | Wagorn et al. |
| 2002/0002525 A1 | 1/2002 | Arai et al. |
| 2002/0026359 A1 | 2/2002 | Long et al. |
| 2002/0035536 A1 | 3/2002 | Gellman |
| 2002/0038282 A1 | 3/2002 | Montgomery |
| 2002/0046099 A1 | 4/2002 | Frengut et al. |
| 2002/0046104 A1 | 4/2002 | Kaddeche et al. |
| 2002/0077891 A1 | 6/2002 | Castle et al. |
| 2002/0099605 A1 | 7/2002 | Weitzman et al. |
| 2002/0111898 A1 | 8/2002 | Numaoka et al. |
| 2002/0123988 A1 | 9/2002 | Dean et al. |
| 2002/0133010 A1 | 9/2002 | Banholzer et al. |
| 2002/0165773 A1 | 11/2002 | Natsuno et al. |
| 2002/0184097 A1 | 12/2002 | Hijiri et al. |
| 2002/0194062 A1 | 12/2002 | Linide |
| 2002/0198780 A1 | 12/2002 | Kawakami et al. |
| 2003/0037334 A1 | 2/2003 | Khoo et al. |
| 2003/0070167 A1 | 4/2003 | Holtz et al. |
| 2003/0083937 A1 | 5/2003 | Hasegawa et al. |
| 2003/0089369 A1* | 5/2003 | Lewis et al. ............ 128/200.23 |
| 2003/0149618 A1 | 8/2003 | Sender et al. |
| 2003/0158145 A1* | 8/2003 | Silk et al. .................... 514/45 |
| 2003/0163372 A1 | 8/2003 | Kolsy |
| 2003/0216963 A1 | 11/2003 | Ishiwaka et al. |
| 2004/0002502 A1* | 1/2004 | Banholzer et al. ...... 514/254.11 |
| 2004/0010003 A1* | 1/2004 | Banholzer et al. ........... 514/291 |
| 2004/0015397 A1 | 1/2004 | Barry et al. |
| 2004/0019523 A1 | 1/2004 | Barry et al. |
| 2004/0044571 A1 | 3/2004 | Bronnimann et al. |
| 2004/0054577 A1 | 3/2004 | Inoue et al. |
| 2004/0054589 A1 | 3/2004 | Nicholas et al. |
| 2004/0059708 A1 | 3/2004 | Dean et al. |
| 2004/0059712 A1 | 3/2004 | Dean et al. |
| 2004/0093327 A1 | 5/2004 | Anderson et al. |
| 2004/0093620 A1 | 5/2004 | Iino et al. |
| 2004/0119740 A1 | 6/2004 | Chang et al. |
| 2004/0143499 A1 | 7/2004 | Dietsch et al. |
| 2004/0143843 A1 | 7/2004 | Khoo et al. |
| 2004/0167928 A1 | 8/2004 | Anderson et al. |
| 2004/0249709 A1 | 12/2004 | Donovan et al. |
| 2005/0065806 A1 | 3/2005 | Harik |
| 2005/0071224 A1 | 3/2005 | Fikes et al. |
| 2005/0096979 A1 | 5/2005 | Koningstein |
| 2005/0131758 A1 | 6/2005 | Desikan et al. |
| 2005/0131762 A1 | 6/2005 | Bharat et al. |
| 2005/0144069 A1 | 6/2005 | Wiseman et al. |
| 2005/0216335 A1 | 9/2005 | Fikes et al. |
| 2005/0222900 A1 | 10/2005 | Fuloria et al. |
| 2005/0222903 A1 | 10/2005 | Buchheit et al. |
| 2005/0222989 A1 | 10/2005 | Haveliwala et al. |
| 2005/0223002 A1 | 10/2005 | Agarwal et al. |
| 2006/0222598 A1 | 10/2006 | Schmidt |

FOREIGN PATENT DOCUMENTS

| | | |
|---|---|---|
| DE | 10050994 A | 4/2002 |
| EP | 1026610 A2 | 8/2000 |
| WO | WO 92 16528 A | 10/1992 |
| WO | 97/01329 A1 | 1/1997 |
| WO | WO 0038074 | 6/2000 |
| WO | 00/69468 A1 | 11/2000 |
| WO | WO 2004/042525 | 5/2004 |

OTHER PUBLICATIONS

Chemical Abstract 82:51342t, vol. 82, No. 9, Mar. 3, 1975—XP 002192833 and XP 002192842.

Chemical Abstract 77:135027, vol. 77, No. 21, Nov. 20, 1972—XP 002192834 and XP 002192843.

Chemical Abstract 128:252519, vol. 128, No. 21, May 25, 1998—XP 002192835 and XP 002192844.

Chemical Abstract 126:292958, vol. 126, No. 22, Jun. 2, 1997—XP 002192836 and XP 002192845.

Chemical Abstract 90:179952, vol. 90, No. 23, Jun. 4, 1979—XP 002192837 and XP 002192846.

Chemical Abstract 85:87108, vol. 85, No. 13, Sep. 27, 1976—XP 002192838 and XP 002192847.

Chemical Abstract 77:28759, vol. 77, No. 5, Jul. 31, 1972—XP 002192839 and XP 002192848.

Chemical Abstract 67:73724, vol. 67, No. 15, Oct. 9, 1967—XP 002192840 and XP 002192849.

Chemical Abstract No. 78:119197 (1973), CAS Registry No. 40797-30-6.

Chemical Abstract No. 118:81214 (1993), CAS Registry No. 53949-94-3.

Chemical Abstract, 59, 1963, 5665 g-h, 5666a.

Chemical Abstract, 61, 1964, 9361 f-h.

Chemical Abstract No. 99:145 (1983).

Chris Sherman, "Google Launches AdWords Select," Feb. 20, 2002, 6 pages.

* cited by examiner

AEROSOL FORMULATION FOR INHALATION COMPRISING AN ANTICHOLINERGIC

RELATED APPLICATIONS

This application claims benefit of U.S. Ser. No. 60/513,862, filed Oct. 23, 2003, and claims priority to German Application No. 103 45 065.3, filed Sep. 26, 2003, each of which is hereby incorporated by reference in its entirety.

FIELD OF THE INVENTION

The present invention relates to pharmaceutical preparations for inhalation containing as the sole active substance a compound of formula 1

$$\text{Me}\underset{N}{\overset{+}{\diagup}}\text{Me} \quad X^-$$

wherein $X^-$ denotes an anion which is preferably selected from among chloride, bromide, iodide, sulfate, phosphate, methanesulfonate, nitrate, maleate, acetate, citrate, fumarate, tartrate, oxalate, succinate, benzoate, and p-toluenesulfonate, as solvent ethanol or mixtures of ethanol and water, at least one pharmacologically acceptable acid and optionally other pharmacologically acceptable excipients and/or complexing agents.

The compounds of formula 1 are known from WO 02/32899 (corresponding to U.S. Pat. No. 6,706,726, which is hereby incorporated by reference). They have valuable pharmacological properties and as highly effective anticholinergics may provide therapeutic benefit in the treatment of respiratory diseases, particularly in the treatment of inflammatory and/or obstructive respiratory diseases, especially in the treatment of asthma or chronic obstructive pulmonary disease (COPD).

The present invention relates to liquid active substance formulations of these compounds which can be administered by inhalation. The liquid formulations according to the invention have to meet high quality standards. The formulations according to the invention may be inhaled orally or nasally. To achieve an optimum distribution of the active substances in the lungs, it is expedient to use a liquid formulation free from propellant gases using suitable inhalers. A formulation of this kind may also be inhaled orally or nasally. Those inhalers which are capable of nebulizing a small amount of a liquid formulation in the dosage needed for therapeutic purposes within a few seconds into an aerosol suitable for therapeutic inhalation are particularly suitable. Within the scope of the invention, preferred nebulizers are those in which an amount of less than 100 microliters, preferably less than 50 microliters, most preferably less than 20 microliters of active substance solution can be nebulized, preferably in one or two puffs, to form an aerosol having an average particle size of less than 20 microns, preferably less than 10 microns, so that the inhalable part of the aerosol already corresponds to the therapeutically effective quantity.

An apparatus of this kind for the propellant-free administration of a metered amount of a liquid pharmaceutical composition for inhalation is described in detail, for example, in WO 91/14468 (corresponding to U.S. Pat. Nos. 5,497,944, and 5,662,271, each of which is hereby incorporated by reference) and herein referred to as a "Weston et al. nebulizer"; and also in WO 97/12687 (corresponding to U.S. Pat. Nos. 5,964,416; 6,402,055; and 6,497,373, each of which is hereby incorporated by reference) herein referred to as a "Jaeger et al. nebulizer A", cf FIGS. 6a and 6b (herein referred to as a "Jaeger et al. nebulizer B") and the accompanying description. In a nebulizer of this kind a pharmaceutical solution is converted by means of a high pressure of up to 600 bar into an aerosol destined for the lungs, which is sprayed. Within the scope of the present specification, reference is expressly made to the entire contents of the literature mentioned above.

In inhalers of this kind the formulations of solutions are stored in a reservoir. It is essential that the active substance formulations used are sufficiently stable when stored and at the same time are such that they can be administered directly, if possible without any further handling, in accordance with their medical purpose. Moreover, they must not contain any ingredients which might interact with the inhaler in such a way as to damage the inhaler or the pharmaceutical quality of the solution or of the aerosol produced.

To nebulize the solution, a special nozzle is used as described for example in WO 94/07607 (corresponding to U.S. Pat. Nos. 5,911,851; 6,007,676; and 6,503,362, each of which is hereby incorporated by reference) or WO 99/16530 (corresponding to U.S. Patent Application Pub. No. 2004/0159319, which is hereby incorporated by reference).

The aim of the present invention is to provide a formulation of the compound of formula 1 which meets the high standards needed in order to allow optimum nebulization of a solution using the inhalers mentioned above. The active substance formulations according to the invention must be of sufficiently high pharmaceutical quality, i.e., they should be pharmaceutically stable over a storage time of some years, preferably at least one year, more preferably two years.

These propellant-free formulations of solutions must also be capable of being nebulized under pressure using an inhaler, the composition delivered by the aerosol produced falling reproducibly within a specified range.

Within the scope of the present invention, those compounds of formula 1 are preferably used wherein the anion $X^-$ is selected from among chloride, bromide, iodide, sulfate, phosphate, methanesulfonate, nitrate, maleate, acetate, citrate, fumarate, tartrate, oxalate, succinate, benzoate, and p-toluenesulfonate.

Preferably, the salts of formula 1 are used wherein $X^-$ denotes an anion selected from the group consisting of chloride, bromide, 4-toluenesulfonate and methanesulfonate.

Particularly preferred, within the scope of the present invention, are the formulations which contain the compound of formula 1 wherein $X^-$ denotes bromide.

References to the compound of formula 1 always include within the scope of the present invention all possible amorphous and crystalline modifications of this compound. References to the compound of formula 1 also include within the scope of the present invention all the possible solvates and hydrates which may be formed from this compound.

Any reference to the compound 1' within the scope of the present invention is to be regarded as a reference to the pharmacologically active cation of the following formula

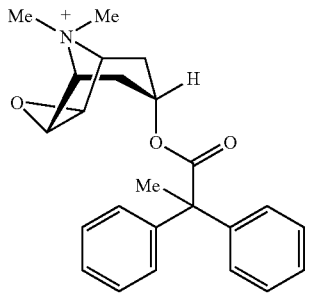

contained in the salts 1.

In the formulation according to the invention the compound 1 is present dissolved in ethanol or in mixtures of ethanol and water.

According to the invention, the formulation preferably contains only a single salt of formula 1. However, the formulation may also contain a mixture of different salts of formula 1. Formulations which contain active substances other than those of formula 1 are not a subject of this invention.

The concentration of the compound of formula 1 based on the proportion of pharmacologically active cation 1' in the pharmaceutical preparation according to the invention is about 4 mg to 2000 mg per 100 mL, according to the invention, preferably about 8 mg to 1600 mg per 100 mL. Particularly preferably, 100 mL of the formulations according to the invention contain about 80 mg to about 1360 mg of 1'.

If the compound of formula 1 used is the particularly preferred compound wherein $X^-$ denotes the bromide, the proportion of 1 according to the invention is about 5 mg to 2500 mg per 100 mL, preferably about 10 mg to 2000 mg per 100 mL of pharmaceutical preparation. Most preferably, 100 mL of the formulations according to the invention contain about 100 mg to 1700 mg of 1.

Formulations according to the invention contain as solvent pure ethanol or mixtures of ethanol and water. If ethanol-water mixtures are used, the mass percentage of ethanol present in these mixtures is preferably in the range from 5% to 99% ethanol, more preferably in the range from 10% to 96% ethanol. Most particularly preferably according to the invention, ethanol-water mixtures used as solvent contain between 50% and 92%, most preferably between 69% and 91% of ethanol.

Other co-solvents may be used apart from ethanol and water. Preferably, however, no other solvents are used according to the invention.

The formulations according to the invention contain pharmacologically acceptable acids organic or inorganic acids for adjusting the pH. The pH of the formulations according to the invention is preferably between 2.5 and 6.5 and more preferably between 3.0 and 5.0, most preferably between about 3.5 and 4.5, according to the invention.

Examples of preferred inorganic acids are selected from the group consisting of hydrochloric acid, hydrobromic acid, nitric acid, sulfuric acid, and phosphoric acid.

Examples of particularly suitable organic acids are selected from the group consisting of ascorbic acid, citric acid, malic acid, tartaric acid, maleic acid, succinic acid, fumaric acid, acetic acid, formic acid, and propionic acid.

Preferred inorganic acids are hydrochloric acid and sulfuric acid, of which hydrochloric acid is particularly preferred according to the invention. Of the organic acids, ascorbic acid, fumaric acid, and citric acid are preferred, citric acid being particularly preferred. If desired, mixtures of the above-mentioned acids may also be used, particularly in the case of acids which have other properties in addition to their acidifying properties, e.g., those which act as flavorings or antioxidants, such as, for example, citric acid or ascorbic acid.

If desired, pharmacologically acceptable bases may be used to titrate the pH precisely. Suitable bases include, for example, alkali metal hydroxides and alkali metal carbonates. The preferred alkali metal ion is sodium. If bases of this kind are used, care must be taken to ensure that the resulting salts, which are then contained in the finished pharmaceutical formulation, are pharmacologically compatible with the above-mentioned acid.

The formulations according to the invention may contain complexing agents as other ingredients. By complexing agents are meant within the scope of the present invention molecules which are capable of entering into complex bonds. Preferably, these compounds should have the effect of complexing cations, most preferably metal cations. The formulations according to the invention preferably contain edetic acid (EDTA) or one of the known salts thereof, e.g., sodium EDTA or disodium EDTA dihydrate, as complexing agent. Preferably, sodium edetate is used, optionally in the form of its hydrates, more preferably in the form of its dihydrate. If complexing agents are used within the formulations according to the invention, their content is preferably in the range from 1 mg to 100 mg per 100 mL, more preferably in the range from 5 mg to 50 mg per 100 mL of the formulation according to the invention. Preferably, the formulations according to the invention contain a complexing agent in an amount of about 6 mg to 30 mg per 100 mL, more preferably about 7 mg to 20 mg per 100 mL of the formulation according to the invention.

The remarks made concerning sodium edetate also apply analogously to other possible additives which are comparable to EDTA or the salts thereof, which have complexing properties and can be used instead of them, such as, for example, nitrilotriacetic acid and the salts thereof.

Other pharmacologically acceptable excipients may also be added to the formulation according to the invention. By adjuvants and additives are meant, in this context, any pharmacologically acceptable and therapeutically useful substance which is not an active substance, but can be formulated together with the active substance in the pharmacologically suitable solvent, in order to improve the qualities of the active substance formulation. Preferably, these substances have no pharmacological effects or no appreciable or at least no undesirable pharmacological effects in the context of the desired therapy. The adjuvants and additives include, for example, stabilizers, antioxidants, and/or preservatives which prolong the shelf life of the finished pharmaceutical formulation, as well as flavorings, vitamins and/or other additives known in the art. The additives also include pharmacologically acceptable salts such as sodium chloride, for example.

The preferred excipients include antioxidants such as ascorbic acid, for example, provided that it has not already been used to adjust the pH, vitamin A, vitamin E, tocopherols, and similar vitamins or provitamins occurring in the human body.

Preservatives can be added to protect the formulation from contamination with pathogenic bacteria. Suitable preservatives are those known from the prior art, particularly benzalkonium chloride or benzoic acid or benzoates such as sodium benzoate in the concentration known from the prior art. Preferably, benzalkonium chloride is added to the formulation according to the invention. The amount of benzalkonium chloride is between 1 mg and 50 mg per 100 mL of formulation, preferably about 7 mg to 15 mg per 100 mL, more preferably about 9 mg to 12 mg per 100 mL of the formulation according to the invention. However, according to the invention, formulations which do not contain any preservatives are particularly preferred.

Preferred formulations contain only benzalkonium chloride, sodium edetate, and the acid needed to adjust the pH in addition to the ethanol or ethanol/water mixtures as solvent and the compounds of formula 1.

The pharmaceutical formulations according to the invention containing compounds of formula 1 are preferably used in an inhaler of the kind described hereinbefore in order to produce the propellant-free aerosols according to the invention. At this point we should once again expressly mention the patent documents described hereinbefore, the contents of which are hereby incorporated by reference.

As described at the beginning, a further developed embodiment of the preferred inhaler is disclosed in WO 97/12687 (cf in particular FIGS. 6a and 6b and the associated passages of description) and is sold under the RESPIMAT® trademark. This RESPIMAT® nebulizer can advantageously be used to produce the inhalable aerosols according to the invention. Because of its cylindrical shape and handy size, this device can be carried anywhere by the patient. The nebulizer sprays a defined volume of the pharmaceutical formulation out through small nozzles at high pressures, so as to produce inhalable aerosols.

The preferred atomizer essentially consists of an upper housing part, a pump housing, a nozzle, a locking mechanism, a spring housing, a spring, and a storage container, characterized by:

a pump housing which is secured in the upper housing part and which comprises at one end a nozzle body with the nozzle or nozzle arrangement, a hollow plunger with valve body, a power takeoff flange in which the hollow plunger is secured and which is located in the upper housing part, a locking mechanism situated in the upper housing part, a spring housing with the spring contained therein, which is rotatably mounted on the upper housing part by means of a rotary bearing, and a lower housing part which is fitted onto the spring housing in the axial direction.

The hollow plunger with valve body corresponds to a device disclosed in WO 97/12687 (corresponding to U.S. Pat. No. 5,964,416). It projects partially into the cylinder of the pump housing and is axially movable within the cylinder. Reference is made in particular to FIGS. 1 to 4, especially FIG. 3, and the relevant parts of the description. The hollow plunger with valve body exerts a pressure of 5 MPa to 60 MPa (about 50 bar to 600 bar), preferably 10 MPa to 60 MPa (about 100 bar to 600 bar) on the fluid, the measured amount of active substance solution, at its high pressure end at the moment when the spring is actuated. Volumes of 10 to 50 microliters are preferred, while volumes of 10 to 20 microliters are particularly preferred and a volume of 15 microliters per spray is most particularly preferred.

The valve body is preferably mounted at the end of the hollow plunger facing the valve body.

The nozzle in the nozzle body is preferably microstructured, i.e. produced by microtechnology. Microstructured valve bodies are disclosed, for example, in WO 94/07607 (corresponding to U.S. Pat. No. 5,911,851, which is hereby incorporated by reference); reference is hereby made to the contents of this specification, particularly FIG. 1 therein and the associated description.

The nozzle body consists, for example, of two sheets of glass and/or silicon firmly joined together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns while the length is preferably 7 to 9 microns.

In the case of a plurality of nozzle openings, preferably two, the directions of spraying of the nozzles in the nozzle body may extend parallel to one another or may be inclined relative to one another in the direction of the nozzle opening. In a nozzle body with at least two nozzle openings at the outlet end the directions of spraying may be at an angle of 20° to 160° to one another, preferably 60° to 150°, most preferably 80° to 100°. The nozzle openings are preferably arranged at a spacing of 10 to 200 microns, more preferably at a spacing of 10 to 100 microns, most preferably 30 to 70 microns. Spacings of 50 microns are most preferred. The directions of spraying will therefore meet in the vicinity of the nozzle openings.

The liquid pharmaceutical preparation strikes the nozzle body with an entry pressure of up to 600 bar, preferably 200 bar to 300 bar, and is atomized into an inhalable aerosol through the nozzle openings. The preferred particle or droplet sizes of the aerosol are up to 20 microns, preferably 3 to 10 microns.

The locking mechanism contains a spring, preferably a cylindrical helical compression spring, as a store for the mechanical energy. The spring acts on the power takeoff flange as an actuating member the movement of which is determined by the position of a locking member. The travel of the power takeoff flange is precisely limited by an upper and lower stop. The spring is preferably biased, via a power step-up gear, e.g. a helical thrust gear, by an external torque which is produced when the upper housing part is rotated counter to the spring housing in the lower housing part. In this case, the upper housing part and the power takeoff flange have a single or multiple V-shaped gear.

The locking member with engaging locking surfaces is arranged in a ring around the power takeoff flange. It consists, for example, of a ring of plastic or metal which is inherently radially elastically deformable. The ring is arranged in a plane at right angles to the atomizer axis. After the biasing of the spring, the locking surfaces of the locking member move into the path of the power takeoff flange and prevent the spring from relaxing. The locking member is actuated by means of a button. The actuating button is connected or coupled to the locking member. In order to actuate the locking mechanism, the actuating button is moved parallel to the annular plane, preferably into the atomizer; this causes the deformable ring to deform in the annual plane. Details of the construction of the locking mechanism are given in WO 97/20590 (corresponding to U.S. Pat. No. 6,453,795, which is hereby incorporated by reference).

The lower housing part is pushed axially over the spring housing and covers the mounting, the drive of the spindle and the storage container for the fluid.

When the atomizer is actuated, the upper housing part is rotated relative to the lower housing part, the lower housing part taking the spring housing with it. The spring is thereby compressed and biased by means of the helical thrust gear and the locking mechanism engages automatically. The angle of rotation is preferably a whole-number fraction of 360°, e.g., 180°. At the same time as the spring is biased, the power takeoff part in the upper housing part is moved along by a given distance, the hollow plunger is withdrawn inside the cylinder in the pump housing, as a result of which some of the fluid is sucked out of the storage container and into the high pressure chamber in front of the nozzle.

If desired, a number of exchangeable storage containers which contain the fluid to be atomized may be pushed into the atomizer one after another and used in succession. The storage container contains the aqueous aerosol preparation according to the invention.

The atomizing process is initiated by pressing gently on the actuating button. As a result, the locking mechanism opens up the path for the power takeoff member. The biased spring pushes the plunger into the cylinder of the pump housing. The fluid leaves the nozzle of the atomizer in atomized form.

Further details of construction are disclosed in PCT Applications WO 97/12683 (corresponding to U.S. Pat. No. 6,176,442, which is hereby incorporated by reference) and WO 97/20590 (corresponding to U.S. Pat. No. 6,176,442), to which reference is hereby made.

The components of the atomizer (nebulizer) are made of a material which is suitable for its purpose. The housing of the atomizer and, if its operation permits, other parts as well are preferably made of plastics, e.g., by injection molding. For medicinal purposes, physiologically safe materials are used.

FIGS. 6a/b of WO 97/12687 show the RESPIMAT® nebulizer which can advantageously be used for inhaling the aqueous aerosol preparations according to the invention.

FIG. 6a (WO 97/12687) shows a longitudinal section through the atomizer with the spring biased while FIG. 6b (WO 97/12687) shows a longitudinal section through the atomizer with the spring relaxed.

The upper housing part (51) contains the pump housing (52) on the end of which is mounted the holder (53) for the atomizer nozzle. In the holder is the nozzle body (54) and a filter (55). The hollow plunger (57) fixed in the power takeoff flange (56) of the locking mechanism projects partially into the cylinder of the pump housing. At its end, the hollow plunger carries the valve body (58). The hollow plunger is sealed off by means of the seal (59). Inside the upper housing part is the stop (60) on which the power takeoff flange abuts when the spring is relaxed. On the power takeoff flange is the stop (61) on which the power takeoff flange abuts when the spring is biased. After the biasing of the spring, the locking member (62) moves between the stop (61) and a support (63) in the upper housing part. The actuating button (64) is connected to the locking member. The upper housing part ends in the mouthpiece (65) and is sealed off by means of the protective cover (66) which can be placed thereon.

The spring housing (67) with compression spring (68) is rotatably mounted on the upper housing part by means of the snap-in lugs (69) and rotary bearing. The lower housing part (70) is pushed over the spring housing. Inside the spring housing is the exchangeable storage container (71) for the fluid (72) which is to be atomized. The storage container is sealed off by the stopper (73) through which the hollow plunger projects into the storage container and is immersed at its end in the fluid (supply of active substance solution). The spindle (74) for the mechanical counter is mounted in the covering of the spring housing. At the end of the spindle facing the upper housing part is the drive pinion (75). The slider (76) sits on the spindle.

The nebulizer described above is suitable for nebulizing the aerosol preparations which may be used according to the invention to produce an aerosol suitable for inhalation.

In another preferred embodiment, the pharmaceutical formulation according to the invention is administered using the nebulizer described above in which a replaceable storage container is used containing the pharmaceutical formulation according to the invention inside a gas- and fluid-tight container as described in WO 99/43571 (corresponding to U.S. Pat. No. 6,685,691, which is hereby incorporated by reference). Some details of the construction of this container will now be described; the reference numerals quoted in the following description correspond to those disclosed in WO 99/43571. The description that follows incorporates the disclosure of WO 99/43571 by reference.

Accordingly, for administering the formulations according to the invention, it is particularly preferable to use a gas- and fluid-tight container as a replaceable cartridge for a medical fluid in a propellant-free atomizer, which, as disclosed in WO 99/43571, comprises a dispensing outlet in the form of a hollow piston, the container comprising:

a foil bag (11, 21, 31) sealed at both ends, at least one end being closed off by a weld seam (13, 23, 32) which runs substantially at right angles to the axis of the bag, and the foil bag is deformable by external pressure at a differential pressure between the interior of the container and its surroundings of less than 300 hPa (300 mbar), an inherently rigid flange (15, 25, 34) which is firmly attached to the foil bag and is constructed as a removable connecting member for fitting the container onto a dispensing outlet (67), a guide channel (42, 54) in the flange, while in the guide channel is formed a sealing point (56, 64, 74) and/or a press fit (55, 66, 77) which surrounds the dispensing outlet, and a removal point for the fluid in the region of the guide channel into which the hollow piston projects during use so as to dip into the medical fluid.

If the formulation according to the invention is nebulized using the method described above (with a RESPIMAT® nebulizer) the quantity delivered should correspond to a defined quantity with a tolerance of not more than 25%, preferably 20% of this amount in at least 97%, preferably at least 98% of all operations of the inhaler (spray actuations). Preferably, between 5 mg and 30 mg of formulation, most preferably between 5 mg and 20 mg of formulation are delivered as a defined mass on each actuation.

However, the formulation according to the invention may also be nebulized by means of inhalers other than those described above, e.g., jet stream inhalers or ultrasound nebulizers. The present invention also relates to an inhalation kit consisting of one of the pharmaceutical preparations according to the invention described above and an inhaler suitable for nebulizing this pharmaceutical preparation. The present invention preferably relates to an inhalation kit consisting of one of the pharmaceutical preparations according to the invention described above and the RESPIMAT® inhaler described above.

The examples of formulations given below serve as illustrations without restricting the subject matter of the present invention to the compositions shown by way of example.

I. EXAMPLES OF FORMULATIONS 100 ml of pharmaceutical preparation contain:

| Example No. | 1 (1'-bromide) (mg) | benzalkonium chloride (mg) | disodium edetate dihydrate (mg) | citric acid (mg) | made up to 100 mL with ethanol/water mixture (% m/m) |
|---|---|---|---|---|---|
| 1 | 2000 | 10 | 10 | 3 | 50/50 |
| 2 | 1000 | 5 | — | 3 | 70/30 |
| 3 | 1500 | — | 10 | 5 | 70/30 |
| 4 | 500 | — | 20 | 2 | 70/30 |
| 5 | 150 | — | 10 | 3 | 90/10 |
| 6 | 250 | — | 10 | 2 | 90/10 |
| 7 | 750 | — | — | 4 | 90/10 |
| 8 | 150 | — | — | 3 | 90/10 |
| 9 | 250 | — | — | 4 | 95/5 |
| 10 | 500 | — | — | 3 | 95/5 |
| 11 | 100 | 5 | — | 3 | 95/5 |

The formulations according to the invention are prepared analogously to methods known in the art, for example, by dissolving the ingredients of the formulation in the solvent ethanol or ethanol/water.

What is claimed is:

1. A pharmaceutical composition comprising:
   (a) an active substance consisting of a compound of formula 1

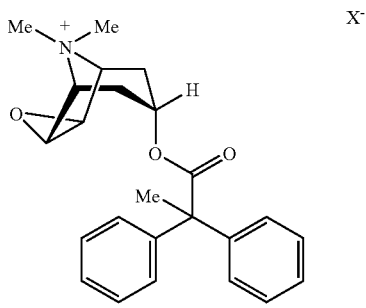

wherein $X^-$ is an anion;
   (b) ethanol or a mixture of ethanol and water; and
   (c) a pharmacologically acceptable acid,
   wherein the composition is propellant-free and has a pH from 2.5 to 6.5.

2. The pharmaceutical composition according to claim 1, further comprising a pharmacologically acceptable excipient or complexing agent.

3. The pharmaceutical composition according to claim 1, wherein $X^-$ is chloride, bromide, iodide, sulfate, phosphate, methanesulfonate, nitrate, maleate, acetate, citrate, fumarate, tartrate, oxalate, succinate, benzoate, or p-toluenesulfonate.

4. The pharmaceutical composition according to claim 1, wherein $X^-$ is chloride, bromide, p-toluenesulfonate, or methanesulfonate.

5. The pharmaceutical composition according to claim 1, wherein component (b) is a mixture of ethanol and water.

6. The pharmaceutical composition according to claim 5, wherein the proportion by mass of ethanol in component (b) is in the range from 5% to 99%.

7. The pharmaceutical composition according to claim 5, wherein the proportion by mass of ethanol in component (b) is in the range from 10% to 96%.

8. The pharmaceutical composition according to one of claims 1 to 7, wherein the pharmacologically acceptable acid is hydrochloric acid, hydrobromic acid, nitric acid, sulfuric acid, phosphoric acid, ascorbic acid, citric acid, malic acid, tartaric acid, maleic acid, succinic acid, fumaric acid, acetic acid, formic acid, or propionic acid.

9. The pharmaceutical composition according to one of claims 1 to 7, wherein the content of 1' is about 4 mg to 2000 mg per 100 mL of the composition.

10. The pharmaceutical composition according to claim 1, further comprising a complexing agent.

11. The pharmaceutical composition according to claim 10, wherein the amount of complexing agent is 1 mg to 100 mg per 100 mL of solution.

12. The pharmaceutical composition according to claim 1, further comprising benzalkonium chloride.

13. The pharmaceutical composition according to claim 10, wherein the amount of benzalkonium chloride is 1 mg to 50 mg per 100 mL of solution.

14. The pharmaceutical composition according to claim 1, wherein the composition has a pH from 3.0 to 5.0.

15. The pharmaceutical composition according to claim 14, wherein the composition has a pH from 3.5 to 4.5.

16. A nebulizer containing the pharmaceutical composition according to one of claims 1 to 7.

* * * * *